(12) United States Patent
Doney

(10) Patent No.: US 10,532,028 B2
(45) Date of Patent: *Jan. 14, 2020

(54) METHOD TO IMPROVE CHARACTERISTICS OF SPRAY DRIED POWDERS AND GRANULATED MATERIALS, AND THE PRODUCTS THEREBY PRODUCED

(75) Inventor: John Alfred Doney, Washington, DC (US)

(73) Assignee: ISP INVESTMENTS LLC, Wilmington, DE (US)

( * ) Notice: Subject to any disclaimer, the term of this patent is extended or adjusted under 35 U.S.C. 154(b) by 2353 days.

This patent is subject to a terminal disclaimer.

(21) Appl. No.: 11/495,993

(22) Filed: Jul. 28, 2006

(65) Prior Publication Data

US 2007/0026083 A1 Feb. 1, 2007

Related U.S. Application Data

(60) Provisional application No. 60/703,374, filed on Jul. 28, 2005.

(51) Int. Cl.
*A61K 9/16* (2006.01)
*A61K 9/48* (2006.01)
*A61K 31/538* (2006.01)
*A61K 31/536* (2006.01)

(52) U.S. Cl.
CPC .................................. *A61K 9/1635* (2013.01)

(58) Field of Classification Search
CPC .. A61K 9/1635; A61K 31/536; A61K 9/1617; A61K 31/538; A61K 9/4866
See application file for complete search history.

(56) References Cited

U.S. PATENT DOCUMENTS

| | | | |
|---|---|---|---|
| 3,981,676 A | 9/1976 | Ghilardi et al. | |
| 4,572,915 A | 2/1986 | Crooks | |
| 4,826,689 A | 5/1989 | Violanto et al. | |
| 4,956,386 A | 9/1990 | McLoughlin et al. | |
| 5,340,591 A | 8/1994 | Nakano et al. | |
| 5,443,842 A | 8/1995 | Seghizzi et al. | |
| 5,519,021 A | 5/1996 | Young et al. | |
| 5,663,169 A | 9/1997 | Young et al. | |
| 5,665,720 A | 9/1997 | Young et al. | |
| 5,811,423 A | 9/1998 | Young et al. | |
| 5,871,775 A | 2/1999 | Valducci | |
| 5,958,458 A * | 9/1999 | Norling et al. | 424/490 |
| 5,989,583 A | 11/1999 | Amselem | |
| 6,056,971 A | 5/2000 | Goldman | |
| 6,143,211 A | 11/2000 | Mathiowitz et al. | |
| 6,184,255 B1 | 2/2001 | Mae et al. | |
| 6,197,349 B1 | 3/2001 | Westesen et al. | |
| 6,221,398 B1 | 4/2001 | Jakupovic et al. | |
| 6,235,224 B1 * | 5/2001 | Mathiowitz et al. | 264/4 |
| 6,262,034 B1 * | 7/2001 | Mathiowitz et al. | 514/44 R |
| 6,300,377 B1 | 10/2001 | Chopra | |
| 6,403,116 B1 | 6/2002 | Anderson et al. | |
| 6,462,093 B1 | 10/2002 | Miyamoto et al. | |
| 6,548,555 B1 | 4/2003 | Curatolo et al. | |
| 6,555,133 B2 | 4/2003 | Makooi-Morehead et al. | |
| 6,579,521 B2 | 6/2003 | Sahner | |
| 6,582,729 B1 | 6/2003 | Eljamal et al. | |
| 6,689,755 B1 | 2/2004 | Gabel et al. | |
| 6,723,359 B2 | 4/2004 | Subramaniam et al. | |
| 6,740,338 B1 | 5/2004 | Chopra | |
| 6,746,635 B2 | 6/2004 | Mathiowitz et al. | |
| 6,763,607 B2 | 7/2004 | Beyerinck et al. | |
| 6,923,988 B2 | 8/2005 | Patel et al. | |
| 6,973,741 B2 | 12/2005 | Beyerinck et al. | |
| 2002/0006443 A1 | 1/2002 | Curatolo et al. | |
| 2002/0009494 A1 | 1/2002 | Curatolo et al. | |
| 2002/0045668 A1 * | 4/2002 | Dang et al. | 514/649 |
| 2003/0049321 A1 | 3/2003 | Begon et al. | |
| 2003/0091643 A1 | 5/2003 | Friesen et al. | |
| 2003/0104063 A1 | 6/2003 | Babcock et al. | |
| 2003/0147965 A1 | 8/2003 | Bassett et al. | |
| 2003/0157182 A1 | 8/2003 | Staniforth et al. | |
| 2003/0170309 A1 | 9/2003 | Babcock et al. | |
| 2003/0224043 A1 | 12/2003 | Appel et al. | |
| 2004/0013734 A1 | 1/2004 | Babcock et al. | |
| 2004/0138299 A1 * | 7/2004 | Cahill et al. | 514/521 |

(Continued)

FOREIGN PATENT DOCUMENTS

EP 1249232 10/2002
GB 988122 4/1965

(Continued)

OTHER PUBLICATIONS

Jirgensons, B. "Solubility and Fractionation of Polyvinylpyrrolidone," Journal of Polymer Science, 1952, vol. VIII, No. 5, pp. 519-527.*

Merriam-Webster's Collegiate Dictionary, 10th edition, Merriam-Webster, Inc.: Springfield, Massachusetts, 1996, pp. 48 (definition of "another").*

Chew, N.Y.K. et al., "Use of Solid Corrugated Particles to Enhance Powder Aerosol Performance," Pharmaceutical Research, vol. 18, No. 11, pp. 1570-1577 (Nov. 2001).

Bain, D.F. et al., "Solvent Influence on Spray-Dried Biodegradable Microspheres," J. Microencapsulation, vol. 16, No. 4, pp. 453-474 (1999).

(Continued)

*Primary Examiner* — Monica A Shin
(74) *Attorney, Agent, or Firm* — Thompson Hine LLP; William Davis

(57) ABSTRACT

A method for preparing solid materials is described. One aspect of the method includes the steps of providing a mixture comprising an organic material in a blend of a solvent and non-solvent for the organic material, distributing the mixture into either droplets or granules, and evaporating the solvent and non-solvent mixture to form particles having an average size of from about 0.5 μm to about 5000 μm.

19 Claims, 11 Drawing Sheets

(56) References Cited

U.S. PATENT DOCUMENTS

| | | |
|---|---|---|
| 2004/0175428 A1 | 9/2004 | Appel et al. |
| 2004/0194338 A1 | 10/2004 | Beyerinck et al. |
| 2004/0220081 A1* | 11/2004 | Kreitz et al. .................. 514/2 |
| 2005/0002870 A1 | 1/2005 | Osborne |
| 2005/0031692 A1 | 2/2005 | Beyerinck et al. |
| 2005/0049223 A1 | 3/2005 | Curatolo et al. |
| 2005/0079138 A1 | 4/2005 | Chickering, III et al. |
| 2005/0133949 A1 | 6/2005 | Stoy |
| 2005/0139144 A1 | 6/2005 | Muller et al. |
| 2005/0143404 A1 | 6/2005 | Rosenberg et al. |
| 2005/0169988 A1 | 8/2005 | Tao et al. |
| 2005/0170000 A1 | 8/2005 | Walker et al. |
| 2005/0170002 A1 | 8/2005 | Kipp et al. |
| 2006/0216351 A1* | 9/2006 | Friesen et al. .................. 424/484 |

FOREIGN PATENT DOCUMENTS

| | | | |
|---|---|---|---|
| GB | 1201171 | | 8/1970 |
| GB | 2401547 | | 11/2004 |
| WO | 97/13503 | | 4/1997 |
| WO | 97/36577 | | 10/1997 |
| WO | 00/40220 | | 7/2000 |
| WO | WO 03/043630 | * | 5/2003 |
| WO | 03/045327 | | 6/2003 |
| WO | 03/049701 | | 6/2003 |
| WO | 03/063821 | | 8/2003 |
| WO | 03/068008 | | 8/2003 |
| WO | 2004/098570 | | 11/2004 |
| WO | 2005/000267 | | 1/2005 |
| WO | 2005/041929 | | 5/2005 |
| WO | 2006/082500 | | 8/2006 |
| WO | 2006/134610 | | 12/2006 |

OTHER PUBLICATIONS

Raula, J. et al., "Influence of the Solvent Composition on the Aerosol Synthesis of Pharmaceutical Polymer Nanoparticles," International Journal of Pharmaceutics, 284, pp. 13-21 (2004).

Hancock, B.C. et al., "Molecular Mobility of Amorphous Pharmaceutical Solids Below Their Glass Transition Temperatures," Pharmaceutical Research, vol. 12, No. 6, pp. 799-806 (1995).

Maa, Yuh-Fun et al., "The Effect of Operating and Formulation Variables on the Morphology of Spray-Dried Protein Particles," Pharmaceutical Development and Technology, 2(3), pp. 213-223 (1997).

Matsuda, Y. et al., "Improvement of the photostability of ubidecarenone microcapsules by incorporating fat-soluble vitamins," International Journal of Pharmaceutics 1985 Netherlands, vol. 26, No. 3, pp. 289-301 (1985).

PCT, International Search Report issued regarding International Application No. PCT/US2006/029821 (published Jun. 21, 2007).

PCT, International Search Report issued regarding International Application No. PCT/US2006/029822 (published May 31, 2007).

PCT, International Search Report issued regarding International Application No. PCT/US2006/029604 (published Feb. 14, 2008).

PCT, International Preliminary Report on Patentability issued regarding International Application No. PCT/US2006/029822 (dated Jan. 29, 2008).

PCT, International Preliminary Report on Patentability issued regarding International Application No. PCT/US2006/029821 (dated Jan. 29, 2008).

PCT, International Preliminary Report on Patentability issued regarding International Application No. PCT/US2006/029604 (dated Jan. 29, 2008).

* cited by examiner

METHOD TO IMPROVE CHARACTERISTICS OF SPRAY DRIED POWDERS AND GRANULATED MATERIALS, AND THE PRODUCTS THEREBY PRODUCED

REFERENCE TO RELATED APPLICATION

This application claims the benefit of U.S. Pat. App. No. 60/703,374, filed Jul. 28, 2005, the contents of which are hereby incorporated by reference.

BACKGROUND OF THE INVENTION

The present invention is directed to methods for improving characteristics of spray dried powders and granulated materials and to the products thereby produced. More particularly, the present invention relates to methods for preparing solid materials utilizing a mixture comprising an organic material in a blend of a solvent and non-solvent for the organic material to produce a spray-dried composition. In accordance with particular embodiments of the invention, the organic material is a polymer.

The selective customization of particle properties can offer intriguing opportunities for production processes and active delivery in a number of industries including pharmaceutical, healthcare, agricultural, personal care, biocide and industrial applications. The morphology of individual particles plays a central role in this pursuit, since morphology directly influences bulk powder properties, such as density, residual solvent content, and flowability. In addition, techniques that modify particle shape and interior structure may profoundly affect product properties, such as active loading, crystallinity, release rate, solubility, and bioavailability. Thus, the ability to design particle morphology has significant implications for the production process and product attributes.

SUMMARY OF THE INVENTION

In accordance with one aspect, the invention provides a method for producing spray-dried powders or granulated products of low residual solvent content from a one-step process. In addition, the resulting powders typically possess higher bulk and tap density than their counterparts produced by conventional methods, due to a change in the particle morphology and size. When applied to produce products incorporating an active ingredient, a system of polymers can be used to modify not only particle morphology, but also the performance properties of the active.

One aspect of the invention involves the pairing of a polymer with a carefully selected solvent blend. This blend comprises a solvent in which the polymer is soluble. The term "soluble" means that the attractive forces between polymer and solvent molecules are greater than the competing inter- and intramolecular attractive forces between polymer molecules. For simplicity, this solvent is simply called "solvent." The solvent blend also contains a solvent for which the opposite is true: The attractive force between polymer and solvent molecules is less than the inter- and intramolecular attractive force between polymer molecules. This second solvent is termed the "non-solvent," because the polymer does not dissolve in it. In accordance with one embodiment of the invention, one polymer and a suitable solvent/non-solvent blend are provided. Additionally, the solvent possesses a lower boiling point than the non-solvent. (Solvent blends at the azeotropic composition can constitute a solvent or non-solvent, but together do not satisfy the criterion of solvent/non-solvent blend.) Preferably, the solvent and non-solvent are miscible. The ratio of solvent to non-solvent is such that the polymer can be considered "dissolved" in the solvent blend.

In another aspect of the invention, the organic material is not polymeric. A non-solvent is selected such that the organic material precipitates from solution during the evaporative loss of the solvent, which boils at a lower temperature than the non-solvent. Differences in organic material solubility between the solvent and non-solvent that accomplish this precipitation during solvent evaporation are within the scope of this invention. Solvent blends at the azeotropic composition can constitute a solvent or non-solvent, but together do not satisfy the criterion of solvent/non-solvent blend.

Unique particle properties can be created by evaporating the solvent blend. For example, this evaporation can occur during the spray drying of the feed solution or granulation processes. Atomized droplets containing a blend of solvents will experience a change in the total solvent composition due to evaporation. The method is independent of how the droplets are generated or atomized. Initially, the organic material exists in a dissolved state, due to a sufficient concentration of solvent in the solution. As the solvent evaporates (it boils at a lower temperature than the non-solvent), the concentration of non-solvent in the droplet increases. Eventually, the non-solvent concentration exceeds the amount required to maintain the organic material in solution. When the organic material comprises a polymer, the polymer collapses from solution and pulls in on itself. This change in polymer conformation can alter the evaporation dynamics of the droplet to create particle morphologies that influence final powder properties. Alternatively, when the organic material does not comprise a polymer, the organic material precipitates during the evaporation process due to the increasing concentration of non-solvent in solution.

This solvent/non-solvent approach can produce a spray dried powder of lower residual solvent content and smaller particle size. A further consequence of this engineered particle morphology in accordance with certain aspects of the invention is the increase in bulk powder density. Increased powder density is an important attribute for many applications, including pharmaceutics, health care, personal care, agriculture, biocide, and industrial chemicals. When the organic material comprises a polymer, the extent of its collapse—and therefore the net effect on the spray dried powder properties—depends on the polymer solvation factors, such as the initial ratio of solvent to non-solvent, the solids concentration in the solution to be spray dried, and the polymer chemical structure and molecular weight. The presence of additional polymers may contribute to the final particle morphology by their interaction with the first polymer and the solvent system.

In addition to reducing residual solvent content and increasing density, when the composition contains an active ingredient, the primary polymer may be paired with the solvent/non-solvent system in order to affect not only the morphology of the particle, but also that of the active, and thereby affect active loading, crystallinity, solubility, stability and release. Additional polymeric adjuvants may be added to serve additional purposes: further inhibit active recrystallization, further maximize active concentration, and further enhance/delay/retard dissolution rate. To accomplish these functionalities, it is necessary to suitably match the adjuvant solubilities with the solvent blend selected for the primary polymer.

DETAILED DESCRIPTION OF THE INVENTION

Figure 1A:
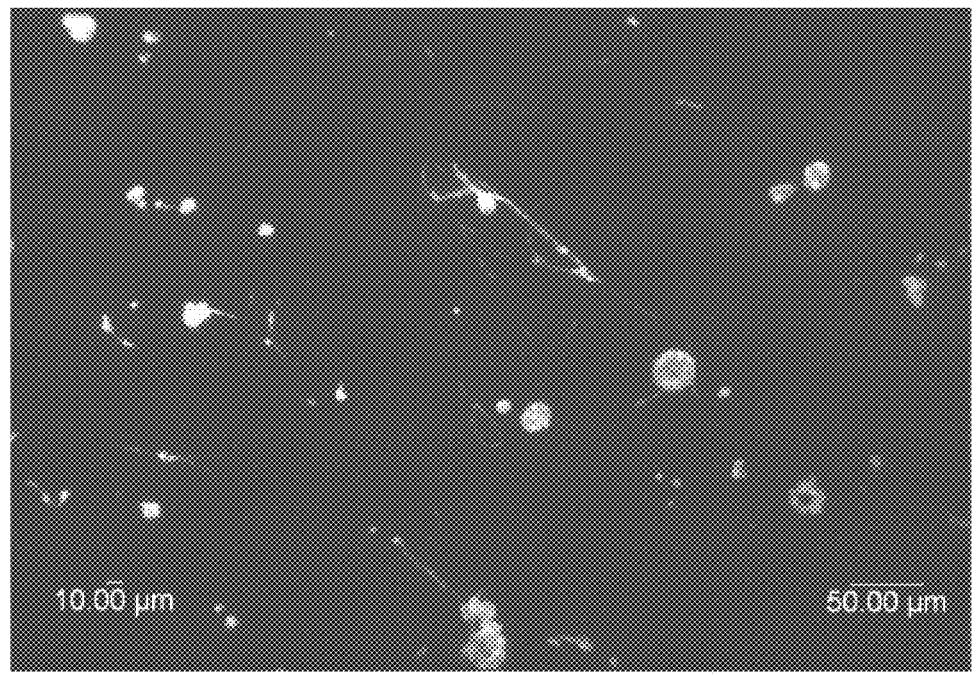
FIGS. 1A-C are photomicrograph images of particles produced in accordance with Example #1.

The term "comprising" encompasses the more restrictive terms "consisting essentially of" and "consisting of."

All percentages, ratios and proportions used herein are by weight unless otherwise specified.

The term "solid dispersion" as used herein refers to a system in a solid state comprising at least two components, wherein one component is dispersed evenly throughout the other component or components. The term "solid dispersion" includes systems having small particles either completely crystalline, completely amorphous or any state in between, typically less than about 1 μm in diameter, of one phase dispersed in another phase.

The term "solid solution" as used herein refers to a type of solid dispersion wherein one component is molecularly dispersed throughout another component such that the system is chemically and physically uniform and homogeneous throughout. These systems do not contain any significant amounts of active ingredients in their crystalline or microcrystalline state as evidenced by thermal analysis or x-ray diffraction.

Although the following description is primarily directed to the preparation of a spray-dried composition, the present invention is not limited to spray-dried compositions. The scope of the present invention also includes methods for preparing other solid materials such as granules and other multiparticulate compositions. These solid materials may comprise any organic matter, such as a sugar, a polymer, an active substance, or mixtures of these materials. Those other solid materials can be prepared in accordance with conventional techniques such as high-shear granulation, fluid bed granulation, film coating or any of their related technologies. In accordance with another aspect of the present invention, the mixture of an organic material in a solvent/non-solvent blend can be applied to a particulate substrate to form coated particles wherein the coating contains the organic material which is preferably in an amorphous state.

In accordance with one embodiment, the present invention is related to a method for preparing a spray-dried composition by providing a mixture containing a polymer in a blend of a solvent and a non-solvent for the polymer and spray drying the mixture to form the spray-dried composition. The spray-dried particles may be useful in a variety of applications including without limitation pharmaceutics, nutraceuticals, health care, personal care, agriculture, biocide and industrial chemicals. In accordance with certain embodiments of the present invention, the spray-dried particles are useful in the formulation of oral, solid-dosage pharmaceutical products. In accordance with other embodiments, powders as small as 0.5 μm suitable for inhalation have been produced. Pharmaceutical spray dried powders in accordance with certain embodiments of the invention typically have a mean particle size of about 0.5 μm-500 μm.

Spray dryer operation influences particle characteristics. Masters (1991) proposes that solvent evaporation from an atomized sphere progresses through three stages: Initially, when the droplet surface is saturated with solvent, evaporation proceeds at a constant rate and is called the first stage of drying. A change in the drying rate is noted with additional drying, due to the formation of dry solids on the surface. At this critical point the surface is no longer considered to be freely saturated with solvent. Further solvent evaporation from the droplet proceeds at a slower rate, requiring diffusion or capillary action through the solid surface layer. At this stage of drying, careful operation of the spray dryer is desirable to remove as much solvent as possible and to avoid expanding the droplet and producing a low density powder. Inlet and outlet temperatures must be controlled, as well as the flow configuration of the drying gas.

Nonetheless, it is sometimes impossible to avoid spray dryer operating conditions that can negatively impact product properties. Formulations containing film formers such as polymers in solvent(s) can quickly reach the critical point of surface evaporation, leading to a situation that approaches or reaches case hardening. Case hardening of the exterior polymer film can make complete or essentially complete solvent removal difficult or essentially impossible without damaging the spray dried powder. The solid polymer (or polymer-like) surface film can also lead to low density powders. Volumetric expansion of trapped solvent due to dryer operation produces low-density, thin-walled particles that are prone to rupture either during the drying step or material handling.

In accordance with one aspect of the invention, a polymer system is provided comprising a polymer—called the primary polymer—and a suitable solvent/non-solvent blend. This approach comprises a solvent in which the polymer is soluble. Guidance in defining polymer solubility is provided by the expansion coefficient ($\alpha$):

$$\alpha = \frac{(\bar{r}^2)^{1/2}}{(\bar{r}_0^2)^{1/2}} \qquad (\S 1)$$

where $\bar{r}^2$ is the mean-square distance between chain ends, and $\bar{r}_o^2$ is the unperturbed dimension. (Equation § 1 can be written for branched polymers in an analogous manner, using square-average radius of gyration about the center of gravity, $\bar{s}^2$, and the corresponding unperturbed dimension, $\bar{s}_o^2$.) Polymer solubility is provided when $\alpha$ is unity or greater, and solvents that satisfy this condition are called "good solvents," or simply "solvents." Solvents uncoil (or expand) the polymer molecule, since the polymer-solvent attractive force is greater than that of polymer-polymer. Light scattering methods, (e.g., Triple Detector Array by Viscotek Corp.), can be used to determine the variables expressed in equation § 1. These concepts are defined in the text *Polymer Chemistry, An Introduction*, by Malcolm P. Stevens, which is incorporated by reference.

When α equals unity, a special condition exists in that polymer-solvent and polymer-polymer forces are balanced. Solvents that enable this condition are called θ solvents. Within the context of this invention, solvents are considered "good solvents" when α is about equal to 1 or more. It is appreciated that temperature influences α, such that a good solvent may be transformed into a non-solvent merely by changing the temperature.

In yet another embodiment of this invention, the solvent blend also contains a solvent for which the opposite is true: Polymer-polymer forces dominate polymer-solvent forces. In this case, α is less than one and the solvent is termed a "non-solvent," because the polymer exists in a collapsed state. In accordance with one embodiment of the invention, one polymer is provided with a suitable solvent/non-solvent blend. The blend of solvent/non-solvent maintains a solvated state of the polymer. Additionally, the solvent possesses a lower boiling point than the non-solvent. (Solvent/non-solvent pairs that form an azeotrope do not satisfy this criterion.) Preferably, the solvent and non-solvent are miscible.

Unique particle properties can be created by evaporating the solvent blend. For example, this evaporation can occur during the spray drying of the feed solution or granulation processes. Atomized droplets containing a blend of solvents will experience a change in the total solvent composition due to evaporation. The method appears to be independent of how the droplets are generated or atomized. Initially, the polymer exists in a solvated state, due to a sufficient amount of the solvent. As it evaporates (the solvent boils at a lower temperature than the non-solvent), the concentration of non-solvent in the droplet increases. Eventually, the solvent composition is insufficient to maintain a solvated polymer. In doing so, the polymer collapses. This change in polymer conformation can alter the evaporation dynamics of the droplet to create particle morphologies that influence final powder properties. Examples of suitable polymer/solvent/non-solvent combinations include, without limitation, polyvinylpyrrolidone (PVP)/dichloromethane/acetone, polyvinylpyrrolidone-co-vinyl acetate (PVP-VA)/acetone/hexane, and ethylcellulose/acetone/water.

In another aspect of the invention, the organic material is not polymeric. A non-solvent is selected such that the organic material precipitates from solution during the evaporative loss of the solvent, which boils at a lower temperature than the non-solvent. Differences in organic material solubility between the solvent and non-solvent that accomplish this precipitation during solvent evaporation are within the scope of this invention. In one embodiment, the organic material solubility is at least about 10-fold greater, more particularly at least about 25-fold greater, still more particularly at least about 50-fold greater in the solvent than in the non-solvent, and in a particularly useful embodiments of the invention, the organic material solubility is at least about 100-fold greater in the solvent than in the non-solvent. Solvent blends at the azeotropic composition can constitute a solvent or non-solvent, but together do not satisfy the criterion of solvent/non-solvent blend.

Unique particle architectures are created by collapse or precipitation of the organic material when the non-solvent concentration exceeds a critical value. This critical ratio $R_c$ can be defined:

$$R_c = \frac{\text{mass nonsolvent}}{\text{mass solvent} + \text{nonsolvent}},$$

which is the maximum fraction of the non-solvent before precipitation occurs. The ratio $R_c$ for a given system can be determined experimentally by identifying the mass fractions of each component that produce a significant increase in solution turbidity. If an $R_c$ value can be identified for a system, then the system comprises a solvent/non-solvent blend. One example is a solution consisting of about 10% (w/w) PVP, 18% (w/w) dichloromethane, and 72% (w/w) acetone, for which $R_c$ equals 0.80. Polymer systems will typically be used at solvent/non-solvent blends that are below the $R_c$ value for the system. It may be advantageous to formulate more complex polymer/solvent systems in order to control particle morphology/size as well as the crystallinity, solubility, bioavailability and/or release characteristics of the active ingredient(s).

The present invention in accordance with other embodiments provides a method to increase the density of spray-dried powders. Typically, spray drying produces sphere-like particles with some degree of interior void. This void increases particle bulk without mass and creates low-density material. Adding a non-solvent to the working solution/dispersion changes the particle size and morphology, leading to an increase in density. Particles may be smaller, wrinkled, dimpled, and/or collapsed compared to those prepared using only solvent. The solvent/non-solvent approach also reduces the mean particle size, allowing the powder to pack better. In addition, powder flow and powder-powder mixing properties are enhanced.

The present invention in accordance with certain aspects provides a method to reduce or eliminate the need for secondary drying of spray-dried powders and granulated materials. These products often contain residual solvent, and it is desirable or necessary to produce a drier product. The high residual solvent content can result from formulation or processing limitations. The general practice has been to use a solvent that dissolves the solids being spray dried. In doing so, solvent can be trapped inside the spray dried powder or granulated bead due to case hardening. The intentional pairing of a lower-boiling solvent with a higher-boiling non-solvent for the materials being processed can yield products of lower residual solvent due to the effect(s) of the non-solvent on the process polymers.

In accordance with certain embodiments of the present invention, a method to reduce crystallinity and increase active concentration is provided. Various solvent evaporation methods (e.g., rotary evaporation, spray drying) have been used to convert crystalline actives to the amorphous form. These methods typically involve formulation of an active/polymer/solvent system. "Good solvents" are invariably selected to dissolve the active and polymer(s). In adopting this approach, however, the type and amount of polymer needed for amorphous conversion is not universal, and sometimes high polymer loading is needed to eliminate active crystallinity. The intentional addition of a non-solvent profoundly and surprisingly affects the degree of activity crystallinity in a wholly different manner.

In an embodiment of the current invention, a non-solvent for the primary polymer is selected that boils at a lower temperature than the solvent. Without being bound to a specific theory, it appears that this non-solvent addition alters the drying dynamics of the system. It has been found that less polymer is needed to achieve amorphous conversion of the crystalline active. Accordingly, these compositions contain a higher concentration of the active than can be produced using solvent-only methods. In accordance with particular embodiments of the present invention, compositions can be prepared from a system comprising a polymer and an active spray dried from a solvent/non-solvent blend that contain more than about 25% active by weight, more particularly more than about 50% active by weight and in accordance with certain embodiments more than about 75% active by weight.

Furthermore, compositions made by the solvent/non-solvent approach are characterized by different dissolution profiles, which may proceed at a faster rate of release or a higher extent of release, or both. In accordance with particular embodiments of the present invention, a composition prepared from a system comprising a polymer and an active spray dried under similar conditions from a solvent/non-solvent system as described herein exhibits a dissolution profile wherein the percent active released at some point in time is at least about 25%, more particularly at least about 50% and in certain cases at least about 100% greater than a control composition prepared from a system comprising the same polymer and active spray dried from the same solvent without the non-solvent. Preferably these limits are obtained within about 120 minutes, more particularly about 60 minutes and still more particularly within about 30 minutes. Dissolution profiles can be determined using test methods as described in the examples.

In a further development of this invention, a polymer system is chosen so that one (or more) polymer(s) work with the solvent/non-solvents to create novel particle morphologies. Additional polymer(s) may be added as needed to affect the solubility and release properties of the active, as well as particle morphology. Enhanced solubility can be achieved by a number of factors, including (but not limited to): improved wettability, creation of amorphous active forms, stabilization against recrystallization, and/or co-solvation effects. In doing so, a supersaturatured solution of the active is produced. "Modified release" refers to changing the time frame in which the active is released, i.e., immediate, delay, extended. These modified releases are created by matching functional polymer(s) with the appropriate solvent/non-solvent blend.

Solvents and non-solvents suitable for use in the process of the present invention can be any organic compound or water in which the organic material is soluble in the case of solvents, or insoluble, in the case of non-solvents. When the organic material does not comprise a polymer, the organic material solubility is about 10-fold greater in the solvent than the non-solvent, and preferably about 100-fold greater in the solvent than the non-solvent. Alternatively, when the organic material comprises one or more polymers, the choice and ratio of solvent/non-solvent depends on the primary polymer selection. Accordingly, the solvent or non-solvent selection depends on the primary polymer. Therefore, a solvent in one system may be a non-solvent in another. Particularly useful solvents and non-solvents include, but are not limited to: acetic acid, acetone, acetonitrile, anisole, 1-butanol, 2-butanol, butyl acetate, tert-butyl-methyl ether, chlorobenzene, chloroform, cumene, cyclohexane, 1-2-dichloroethane, dichloromethane, 1-2-dimethoxyethane, N—N-dimethylacetamide, N—N-dimethylformamide, 1-4-dioxane, ethanol, 2-ethoxyethanol, ethyl acetate, ethylene glycol, ethyl ether, ethyl formate, formamide, formic acid, heptane, hexane, isobutyl acetate, isopropyl acetate, methanol, methyl acetate, 2-methoxyethanol, 3-methyl-1-butanol, methylbutylketone, methylcyclohexane, methylethyl ketone, methylisobutyl ketone, 2-methyl-1-propanol, N-methylpyrrolidone, nitromethane, pentane, 1-pentanol, 1-propanol, 2-propanol, propyl acetate, pyridine, sulfolane, tetrahydrofuran, tetralin, 1-2-2-trichloroethene, toluene, water, and xylene. Mixtures of solvents and mixtures of non-solvents can also be used. Azeotropic blends of solvents (which boil at one common temperature) can comprise either the solvent or non-solvent, but not the solvent/non-solvent blend.

Primary polymers and other organic materials that are suitable for use in the mixtures of the present invention should be soluble in the solvent and not soluble in the non-solvent. Specific examples of useful organic materials include, but are not limited to: aliphatic polyesters (e.g., poly D-lactide), sugar alcohols (e.g., sorbitol, maltitol, isomalt), carboxyalkylcelluloses (e.g., carboxymethylcellulose and crosslinked carboxymethylcellulose), alkylcelluloses (e.g., ethylcellulose), gelatins, hydroxyalkylcelluloses (e.g., hydroxymethylcellulose), hydroxyalkylalkylcelluloses (e.g., hydroxypropylmethyl cellulose), hydroxyalkylalkylcellulose derivatives (e.g. hydroxypropylmethyl cellulose acetate succinate, hydroxypropylmethyl cellulose phthalate) polyamines (e.g., chitosan), polyethylene glycols (e.g., PEG 8000, PEG 20000), methacrylic acid polymers and copolymers (e.g., Eudragito series of polymers of Rohm Pharma GmbH), homo- and copolymers of N-vinyl pyrrolidone (e.g., polyvinylpyrrolidone, crosslinked polyvinylpyrrolidone and polyvinylpyrrolidone-co-vinyl acetate), homo- and copolymers of vinyllactam, starches (e.g. cornstarch, sodium starch glycolate), polysaccharides (e.g., alginic acid), poly glycols (e.g., polypropylene glycol, polyethylene glycol), polyvinyl esters (e.g., polyvinyl acetate), refined/modified shellac. The amount of the polymer or organic material present in the mixture may range from about 1% to about 95%, more particularly from about 5% to 90%, by weight of the mixture. Blends of organic materials may also be used.

The spray-dried mixture may also include an active material. Although the following description is primarily directed to pharmaceutically active materials, the present invention is not limited to pharmaceutically active materials. The scope of the present invention also includes active ingredients used in the personal care (e.g., hair care, skin care or oral care), agriculture, biocide and other industrial or consumer applications. As used herein "pharmaceutically active materials" is intended to include nutritionally active materials, dietary supplements, and vitamin materials. The mixture may contain from about 1% to about 95% active, more particularly from about 20% to about 80% active, depending on the desired dose of the active. Actives that can be used in accordance with the present invention are not particularly limited. Examples of actives that may be used include, but are not limited to: abacavir sulfate, acebutolol, acetaminophen, acemetacin acetylcysteine, acetylsalicylic acid, acyclovir, adefovir dipivoxil, alprazolam, albumin, alfacalcidol, allantoin, allopurinol, ambroxol, amikacin, amiloride, aminoacetic acid, amiodarone, amitriptyline, amlodipine, amoxicillin, amoxicillin trihydrate, amiodarone hydrochloride, amphotericin B, ampicillin amprenavir, aprepitant, anastrozole, ascorbic acid, aspartame, astemizole, atazanavir sulfate, atenolol, atorvastatin calcium, azathioprine, azithromycin, azithromycin dihydride, beclomethasone, benserazide, benzalkonium hydroxide, benzocaine, benzoic acid, betametasone, bezafibrate, bicalutamide, biotin, biperiden, bisoprolol, bosentan, bromazepam, bromhexine, bromocriptine, budesonide, bufexamac, buflomedil, buspirone, caffeine, camphor, candesartan cilexetil, captopril, carbamazepine, carbidopa, carboplatin, carvedilol, cefachlor, cefalexin, cefadroxil, cefazolin, cefdinir, cefixime, cefotaxime, ceftazidime, ceftriaxone, cefuroxime, celecoxib, chloramphenicol, chlorhexidine, chlorpheniramine, chlortalidone, choline, cilastatin, cilostazol, cimetidine, ciprofloxacin, cisapride, cisplatin, citalopram hydrobromide, clarithromycin, clavulanic acid, clomipramine, clonazepam, clonidine, clopidogrel bisulfate, clotrimazole, clozapine, codeine, colestyramine, coenzyme Q10, cromoglycic acid, cyanocobalamin, cyclosporin, cyproterone, danazole, delavirdine mesylate, desipramine, desloratadine, desmopressin, desogestrel, dexamethasone, dexpanthenol, dextromethorphan, dextropropoxiphene, diazepam, diclofenac, digoxin, dihydrocodeine, dihydroergotamine, diltiazem, diphenhydramine, dipyridamole, dipyrone, disopyramide, docetaxel, domperidone, dopamine, doxycycline, doxorubicin hydrochloride, dronabinol, dutasteride, efavirenz, eletriptan hydrobromide, emtricitabine, enalapril, enrofloxacin, entacapone, ephedrine, epinephrine, eplerenone, eprosartan mesylate, ergocalciferol, ergoloid mesylate, ergotamine tartrate, erythromycin, escitalopram oxalate, estradiol, ethinylestradiol, etoposide, exemestane, ezetimibe, famotidine, felodipine, fenofibrate, fenoterol, fentanyl, fexofenadine hydrochloride, finasteride, flavin mononucleotide, fluconazole, flunarizine, fluorouracil, fluoxetine, flurbiprofen, fluphenazine hydrochloride, flutamide, fluticasone propionate, fluvastatin, fosamprenavir, fosamprenavir calcium, furosemide, gabapentin, galantamine hydrobromide, ganciclovir, gemfibrozil, gentamicin, *Ginkgo biloba*, glibenclamide, glimepiride, glipizide, *Glycyrrhiza glabra*, glyburide, guaifenesin, guanabenz, haloperidol, heparin, hyaluronic acid, hydrochlorothiazide, hydrocodone, hydrocortisone, hydromorphone, hydroxytetracycline, ipratropium hydroxide, ibuprofen, idarubicin, imipenem, imipramine hydrochloride, indinavir sulfate, indomethacin, iohexol, iopamidol, irinotecan, isosorbide dinitrate, irbesartan, isosorbide mononitrate, isotretinoin, isradipine, itraconazole, ketotifen, ketoconazole, ketoprofen, ketorolac, labetalol, lactulose, lamivudine, lamotrigine, lansoprazole, lecithin, levetiracetam, levocarnitine, levodopa, levoglutamide, levonorgestrel, levothyroxine, lidocaine, lipase, lisinopril, loperamide, lopinavir, loratadine, lorazepam, lovastatin, medroxyprogesterone, meloxicam, melphalan, menthol, mercaptopurine, mesalamine, methotrexate methyldopa, N-methylephedrine, methylprednisolone, metoclopramide, metolazone, metoprolol, miconazole, midazolam, minocycline, minoxidil, misoprostol, mitotane, modafanil, mometasone, morphine, mosapride, multivitamins and minerals, nabumetone, nadolol, naftidrofuryl, naproxen, nefazodone, nelfinavir mesylate, neomycin, nevirapine, nicardipine hydrochloride, nicergoline, nicotinamide, nicotine, nicotinic acid, nifedipine, nimodipine, nisoldipine, nitrendipine, nizatidine, norethisterone, norfloxacin, norgestrel, nortriptyline, nystatin, ofloxacin, olanzepine, olmesartan medoxomil, omeprazole, ondansetron, orlistat, oxcarbazepine, paclitaxel, pancreatin, panthenol, pantoprazole, pantothenic acid, paracetamol, paroxetine hydrochloride, penicillin G, penicillin V, perphenazine, phenobarbital, phenylephrine, phenylpropanolamine, phenytoin, pimecrolimus, pimozide, pioglitazone hydrochloride, piroxicam, polymyxin B, povidone-iodine, pravastatin sodium, prazepam, prazosin, prednisolone, prednisone, proglumetacin, propafenone hydrochloride, propranolol, propofol, pseudoephedrine, pyridoxine, quinaprile hydrochloride, quinidine, raloxifine hydrochloride, ramipril, ranitidine, reserpine, retinol, ribavirin, riboflavin, rifampicin, risperidone, ritonavir, rosuvastatin calcium, rutoside, saccharin, salbutamol, salcatonin, salicylic acid, salmetrol xinafoate, saquinavir, sertaline, sildenafil citrate, simvastatin, sirolimus, somatropin, sotalol, spironolactone, stavudine, sucralfate, sulbactam, sulfamethoxazole, sulphasalazine, sulpiride, tacrolimus, tadalafil, tamoxifen, tamsulosin hydrochloride, tegafur, tenofovir disoproxil fumarate, tenoxicam, teprenone, terazosin, terbinafine hydrochloride, tegaserod maleate, telmisartan, terbutaline, terfenadine, thalidomide, theophylline, thiamine, tiaprofenic acid, ticlopidine, timolol, tizanidine hydrochloride, topiramate, trandolapril, tranexamic acid, tretinoin, triamcinolone acetonide, triamterene, triazolam, trimethoprim, troxerutin, uracil, valdecoxib, valgancyclovir hydrochloride, valproic acid, valrubicin, valsartan, vancomycin, verapamil, vardenafil hydrochloride, vitamin E, zafirlukast, zalcitabine, zalephon, zidovudine, ziprasidone, zolpidem tartrate, zonisamide, zotepine.

The spray-dried mixture may also contain additional organic materials that can modify properties of the spray-dried composition. For example, certain organic substances can be included to control particle morphology/size as well as the solubility, bioavailability and release characteristics of the active ingredient. Additional organic material may also be included in the mixture to further inhibit active recrystallization, further maximize active concentration and further enhance/delay/retard dissolution rate. Additional organic materials that can be incorporated into this system are not particularly limited. In one embodiment of this invention the additional organic material is polymeric.

The mixture to be spray dried typically contains from about 40% to 99.9% by weight total solvent/non-solvent, more particularly from about 80% to 95% by weight total solvent/non-solvent based on the total weight of the mixture. The critical ratio $R_c$ can vary from about 0.01-0.99, more particularly from about 0.1-0.9, still more particularly from about 0.3-0.8.

In addition to the solvent, polymer and any active, the mixture to be spray dried may also include other ingredients to improve performance, handling or processing of the mixture. Typical ingredients include, but are not limited to, surfactants, pH modifiers, fillers, complexing agents, solubilizers, pigments, lubricants, glidants, flavor agents, plasticizers, taste masking agents, etc., which may be used for customary purposes and in typical amounts.

The spray-drying apparatus used in the process of the present invention can be any of the various commercially available apparatus. Examples of specific spray-drying devices include spray dryers manufactured by Niro, Inc. (e.g., SD-Micro®, PSD®-1, PSD®-2, etc.), the Mini Spray Dryer (Buchi Labortechnik AG), spray dryers manufactured by Spray Drying Systems, Inc. (e.g., models 30, 48, 72), and SSP Pvt. Ltd.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954). The contents of these references are hereby incorporated by reference.

The term "spray-drying" is used conventionally and, in general, refers to processes involving breaking up liquid mixtures into small droplets and rapidly removing solvent from the mixture in a container (spray-drying apparatus) where there is a strong driving force for evaporation of solvent from the droplets. Atomization techniques include two-fluid and pressure nozzles, and rotary atomizers. The strong driving force for solvent evaporation is generally provided by maintaining the partial pressure of solvent in the spray-drying apparatus well below the vapor pressure of the solvent at the temperatures of the drying droplets. This may be accomplished by either (1) maintaining the pressure in the spray-drying apparatus at a partial vacuum; (2) mixing the liquid droplets with a warm drying gas; or (3) both.

Generally, the temperature and flow rate of the drying gas and the design of the spray dryer are chosen so that the atomized droplets are dry enough by the time they reach the wall of the apparatus that they are essentially solid and so that they form a fine powder and do not stick to the apparatus wall. The actual length of time to achieve this level of dryness depends on the size of the droplets, the formulation, and spray dryer operation. Following the solidification, the solid powder may stay in the spray-drying chamber for 5-60 seconds, further evaporating solvent from the solid powder. The final solvent content of the particle as it exits the dryer should be low, since this improves the handling and stability of the product. Generally, the residual solvent content of the spray-dried composition should be less than about 10% by weight and preferably less than about 2% by weight. Although not typically required in accordance with the present invention, because the presence of a non-solvent produces a spray-dried powder of lower residual solvent content, it may be useful in accordance with certain embodiments of the present invention to subject the spray-dried composition to further drying to lower the residual solvent to even lower levels. Additional detail with respect to a particular spray-drying process is described in more detail in the examples. However, the operating conditions to spray dry a powder are well known in the art and can be easily adjusted by the skilled artisan. Furthermore, the examples describe results obtained with a laboratory scale spray dryer. One of ordinary skill in the art would readily appreciate the variables that must be modified to obtain similar results with a production scale unit.

Compositions of the invention may be presented in numerous forms commonly used in a wide variety of industries. Exemplary presentation forms are powders, granules, and multiparticulates. These forms may be used directly or further processed to produce tablets, capsules, or pills, or reconstituted by addition of water or other liquids to form a paste, slurry, suspension or solution. Various additives may be mixed, ground, or granulated with the compositions of this invention to form a material suitable for the above product forms.

Compositions of the invention may be formulated in various forms so that they are delivered as a suspension of particles in a liquid vehicle. Such suspensions may be formulated as a liquid or as a paste at the time of manufacture, or they may be formulated as a dry powder with a liquid, typically water, added at a later time but prior to use. Such powders that are constituted into a suspension are often referred to as sachets or oral powders for constitution (OPC). Such product forms can be formulated and reconstituted via any known procedure.

In pharmaceutical applications, compositions of the present invention may be delivered by a wide variety of routes, including, but not limited to, oral, nasal, rectal, vaginal, subcutaneous, intravenous, and pulmonary. Generally, the oral route is preferred.

Oral, solid-dose pharmaceutical spray dried powders typically have a mean particle size of about 0.5 μm-500 μm and are generally prepared from solutions at concentrations of 1% or more total solids, more particularly from about 2-50%, and still more particularly from about 3-25% solids.

Oral, solid dose pharmaceutical granules typically have a mean particle size of about 50 μm-5000 μm. Techniques to produce granules include, but are not limited to, wet granulation and various fluid bed granulating methods.

The present invention is described in more detail by the following non-limiting examples.

EXAMPLES

A. Example #1

1. Polyvinylpyrrolidone (PVP) (Plasdone® K-29/32, International Specialty Products) (10% by weight) solutions were spray dried from a single solvent solution and two solvent/non-solvent blend solutions with different solvent/non-solvent ratios. Solvent was dichloromethane, non-solvent was acetone.

2. Spray drying was conducted on an SD-Micro® (Niro, Inc.) spray dryer, and experimental conditions were maintained constant other than solvent composition of the solution to be spray dried.

3. Residual solvent content:

| APPROACH | SOLVENT | RESIDUAL SOLVENT |
|---|---|---|
| conventional | 100% solvent | 8.0% |
| experimental, #1 | 60% solvent + 40% non-solvent | 7.3% |
| experimental, #2 | 20% solvent + 80% non-solvent | 5.4% |

Figure 1B:
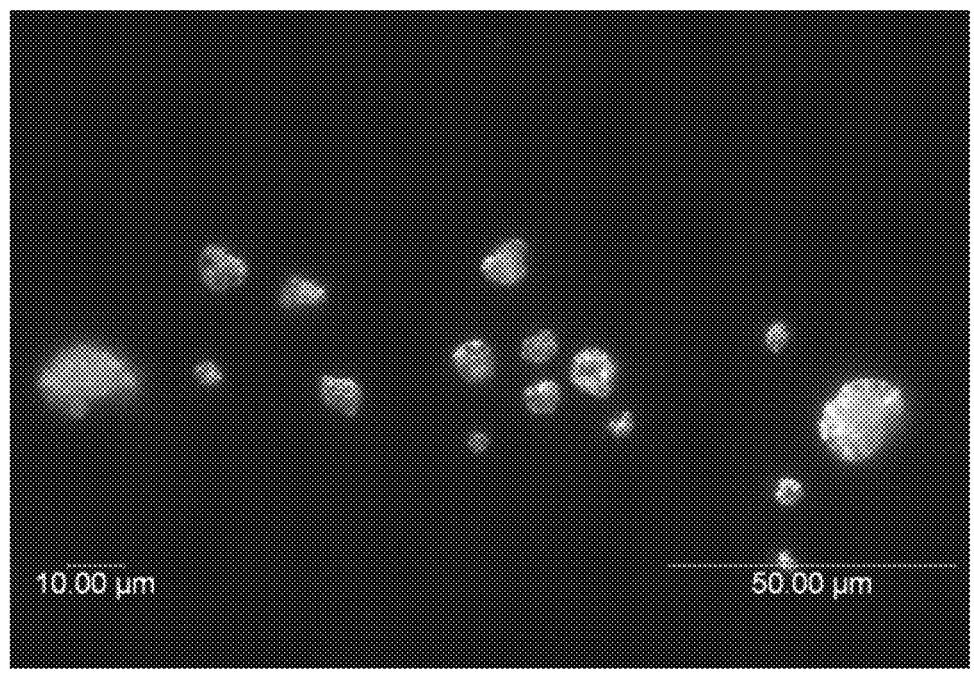
Figure 1C:
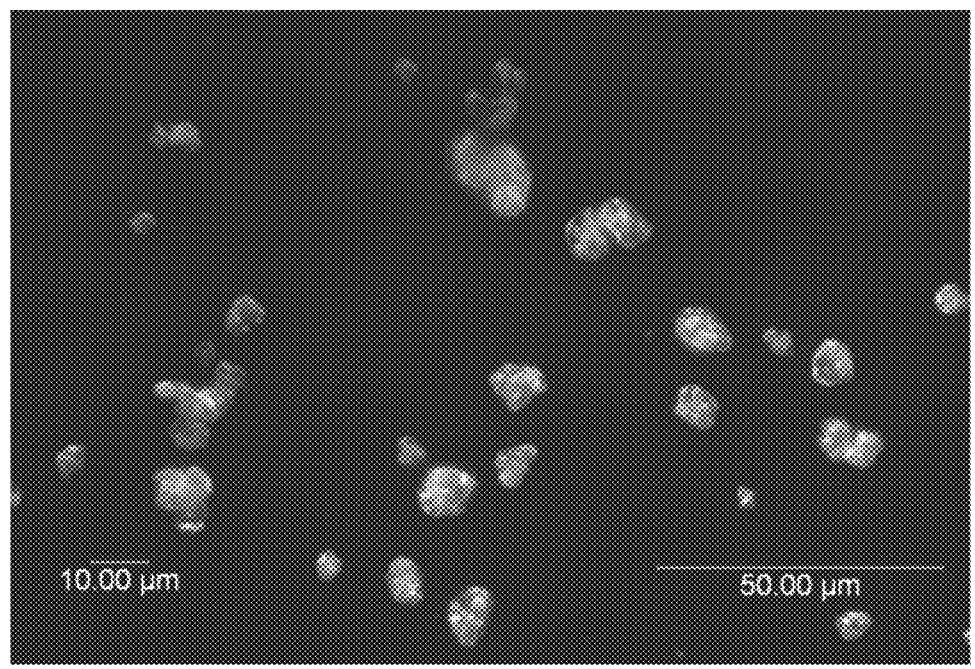

4. Particle morphology
   a. From solvent: spheres and thread-like tails due to viscous effects as shown in FIG. 1A.
   b. From solvent/non-solvent: smaller, non-spherical particles with increasing shape irregularity as non-solvent content increases (FIGS. 1B and 1C), loss of viscous threads that were observed in the 100% solvent experiment.

B. Example #2

1. Polyvinylpyrrolidone (PVP) (Plasdone® K-29/32, International Specialty Products) (10% by weight) was spray dried from a solvent blend of 60% solvent/40% non-solvent with and without added methacrylic acid copolymer (Eudragit® E100, Rohm Pharma GmbH) as second added polymer. Solvent was dichloromethane, non-solvent was acetone.

2. Spray drying was conducted on an SD-Micro® (Niro, Inc.) spray dryer under identical experimental conditions other than the addition of the second polymer.

3. Results:
    a. Residual solvent content:

| RATIO PVP:METHACRYLIC ACID COPOLYMER | RESIDUAL SOLVENT |
|---|---|
| 1:2 | 1.0% |
| 1:0 | 2.4% |

C. Example #3

Figure 2A:
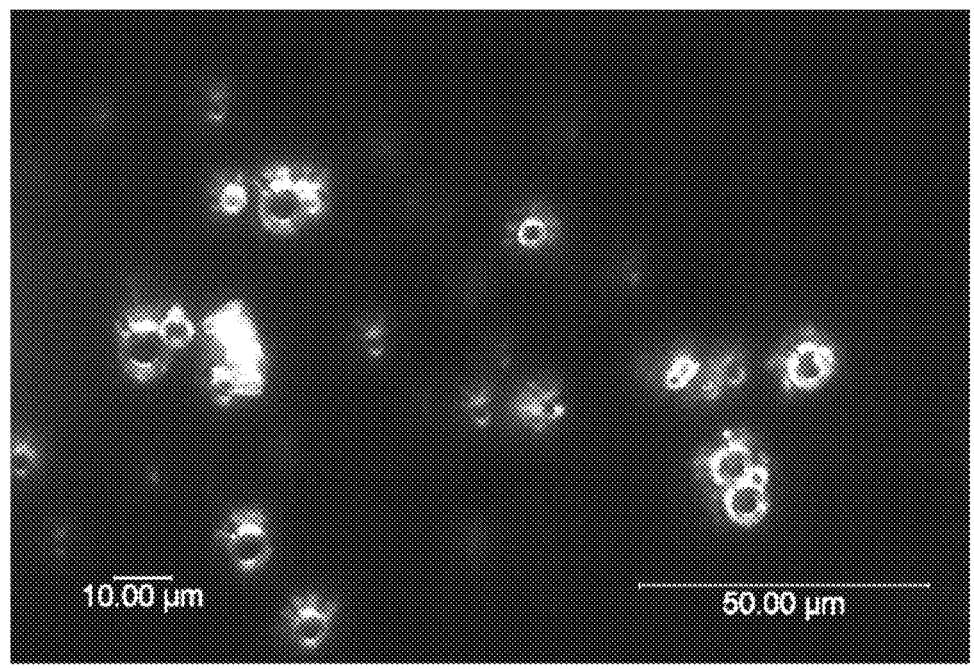
FIGS. 2A-B are photomicrograph images of particles produced in accordance with Example #3.
Figure 2B:
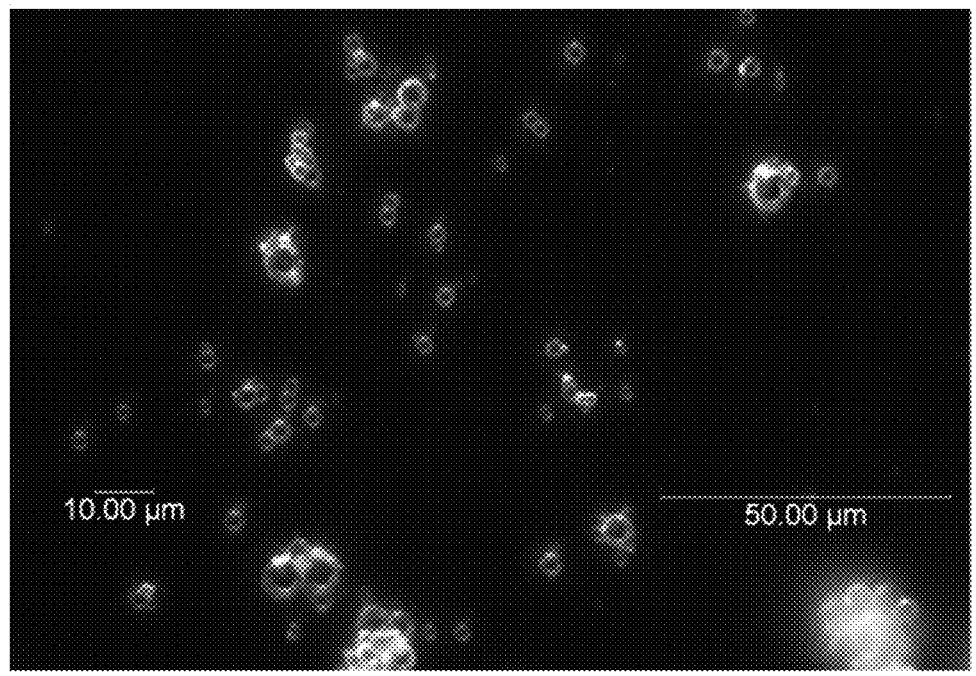
Figure 3:
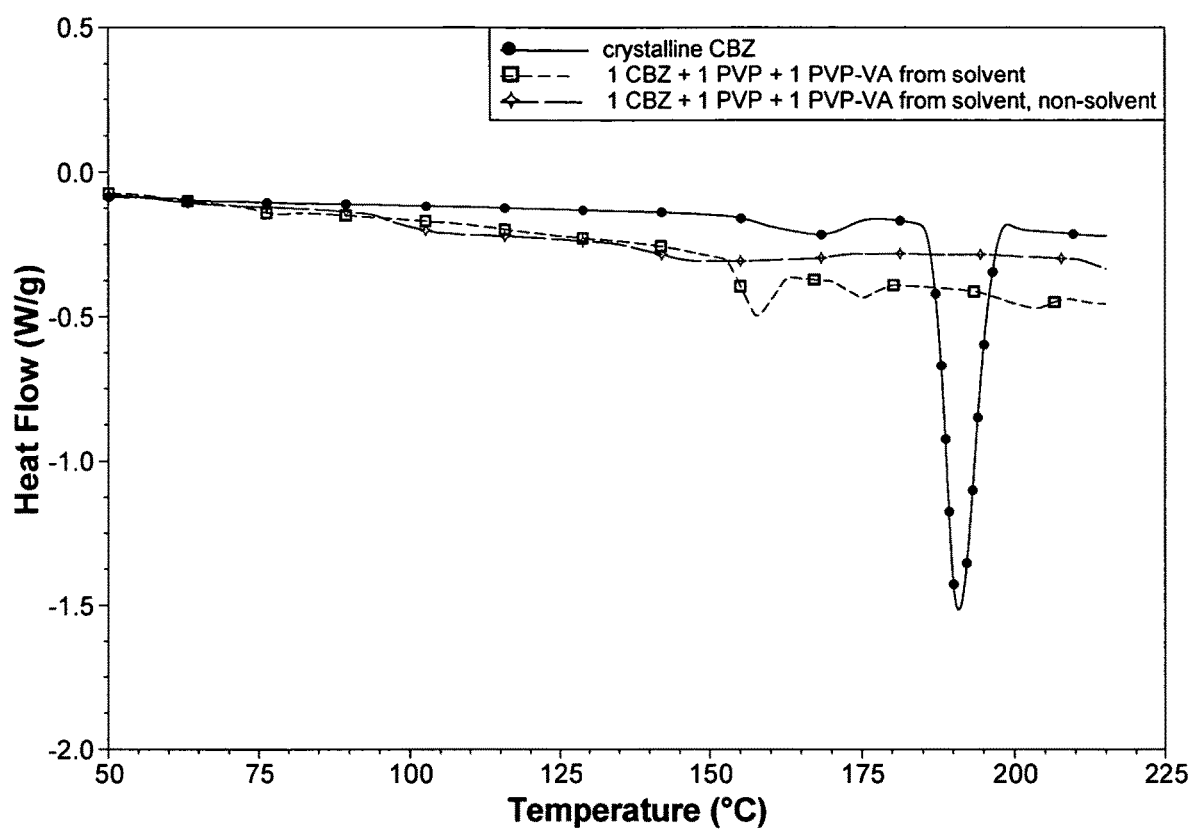
FIG. 3 is a plot of heat flow versus temperature for the particles produced in accordance with Example #3.

1. 1 part Carbamazepine (CBZ) was spray dried with 1 part polyvinylpyrrolidone (PVP) (Plasdone® K-29/32, International Specialty Products) and 1 part polyvinylpyrrolidone-co-vinyl acetate (PVP-VA) (Plasdone® S-630, International Specialty Products) from solvent and solvent/non-solvent solutions at 10% solids by weight. Solvent was dichloromethane (20%), non-solvent was acetone (80%).
2. Spray drying was conducted on an SD-Micro® (Niro, Inc.) spray dryer under identical experimental conditions other than solvent composition.
3. Results:
    a. CBZ from solvent solution
        1) Particle morphology: spherical as shown in FIG. 2A.
        2) Particle size (from optical microscopy): 10 μm
        3) Residual solvent immediately after spray drying: 3.2%
        4) Bulk density: 0.041 g/mL
        5) Density after 1250 taps: 0.064 g/mL
        6) Product contained polymorphic forms of crystalline CBZ, as detected by modulated differential scanning calorimetry (MDSC) and shown in FIG. 3.
    b. CBZ from solvent/non-solvent solution
        1) Particle morphology: spherical as shown in FIG. 2B.
        2) Particle size (from optical microscopy): 3 μm-5 μm
        3) Residual solvent immediately after spray drying: 2.0%
        4) Bulk density: 0.057 g/mL
        5) Density after 1250 taps: 0.18 g/mL
        6) Spherical morphology was unexpected, based on previous examples, expected particles to be dimpled, raisin-like, or folded. Presence of second polymer modified particle morphology to create spherical particles.
        7) Residual crystallinity was not detected by MDSC (FIG. 3)

D. Example #4

Figure 4A:
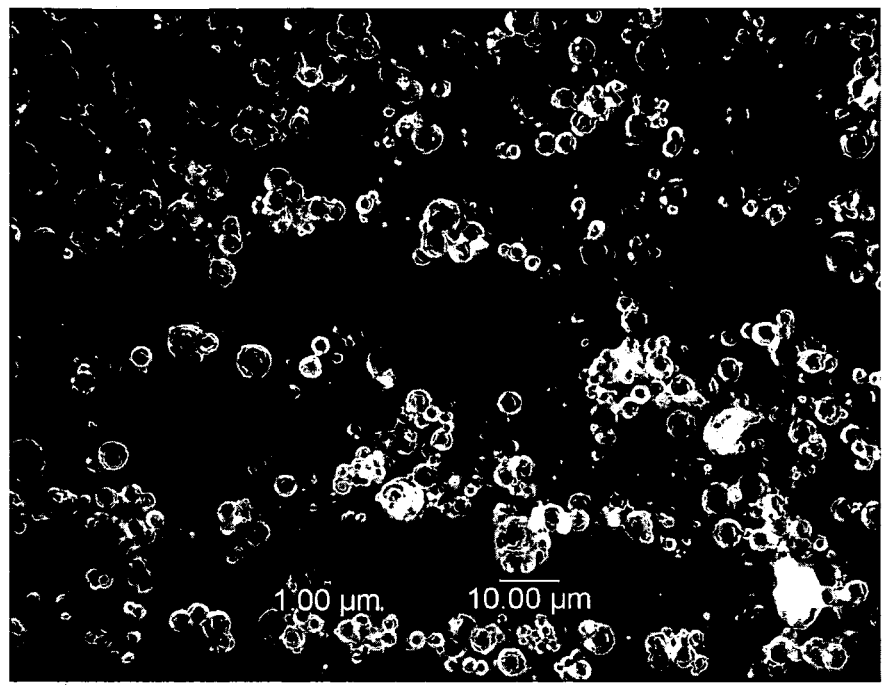
FIGS. 4A-B are photomicrograph images of particles produced in accordance with Example #4.
Figure 4B:
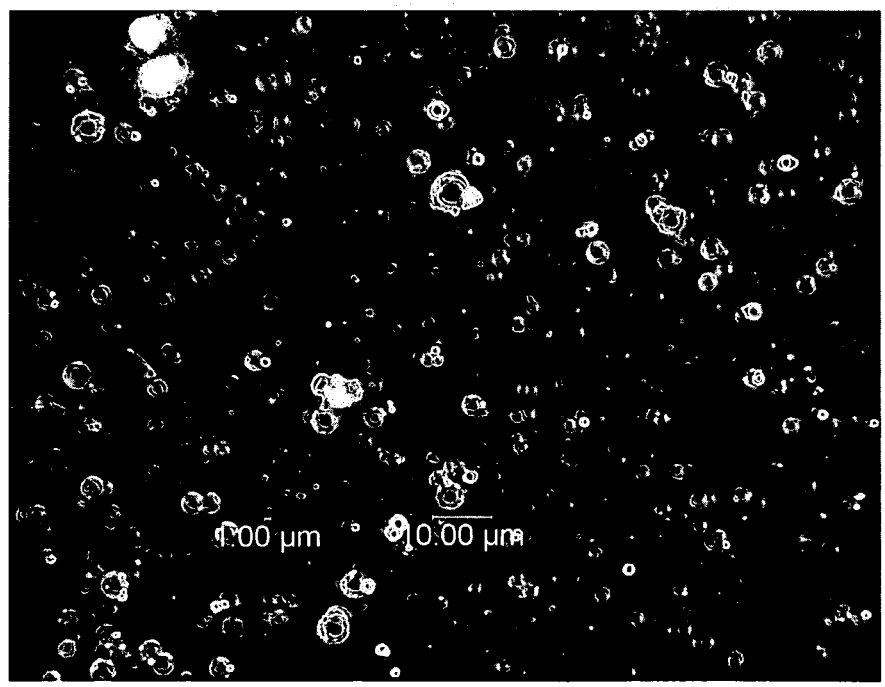

1. One part efavirenz (EFV) with three parts polyvinylpyrrolidone-co-vinyl acetate (PVP-VA) (Plasdone® S-630, International Specialty Products) was spray dried from solvent and solvent/non-solvent solutions at 10% solids by weight. Solvent was acetone (33%), non-solvent was hexane (66%).
2. Spray drying was conducted on an SD-Micro® (Niro, Inc.) spray dryer under identical experimental conditions other than solvent composition.
3. Results:
    a. EFV from solvent only solution
        1) Particle morphology: spherical, as shown in FIG. 4A
        2) Particle size (from optical microscopy): 5 μm
        3) Bulk density: 0.13 g/mL
        4) Density after 1250 taps: 0.21 g/mL
    b. EFV from solvent/non-solvent solution
        1) Particle morphology: spherical, as shown in FIG. 4B
        2) Particle size (from optical microscopy): 1 μm
        3) Bulk density: 0.28 g/mL
        4) Density after 1250 taps: 0.47 g/mL

E. Example #5

1. Efavirenz (EFV) was spray dried with a solubility-enhancing polymer in the ratio 1 EFV:3 polyvinylpyrrolidone (PVP) (Plasdone® K-29/32, International Specialty Products) with 2% sodium lauryl sulfate (dry weight basis) from solvent and solvent/non-solvent solutions. Dichloromethane was the solvent and acetone was the non-solvent.

| formula | solvent composition |
|---|---|
| 5a | 100% solvent |
| 5b | 20% non-solvent, 80% solvent |

Figure 5:
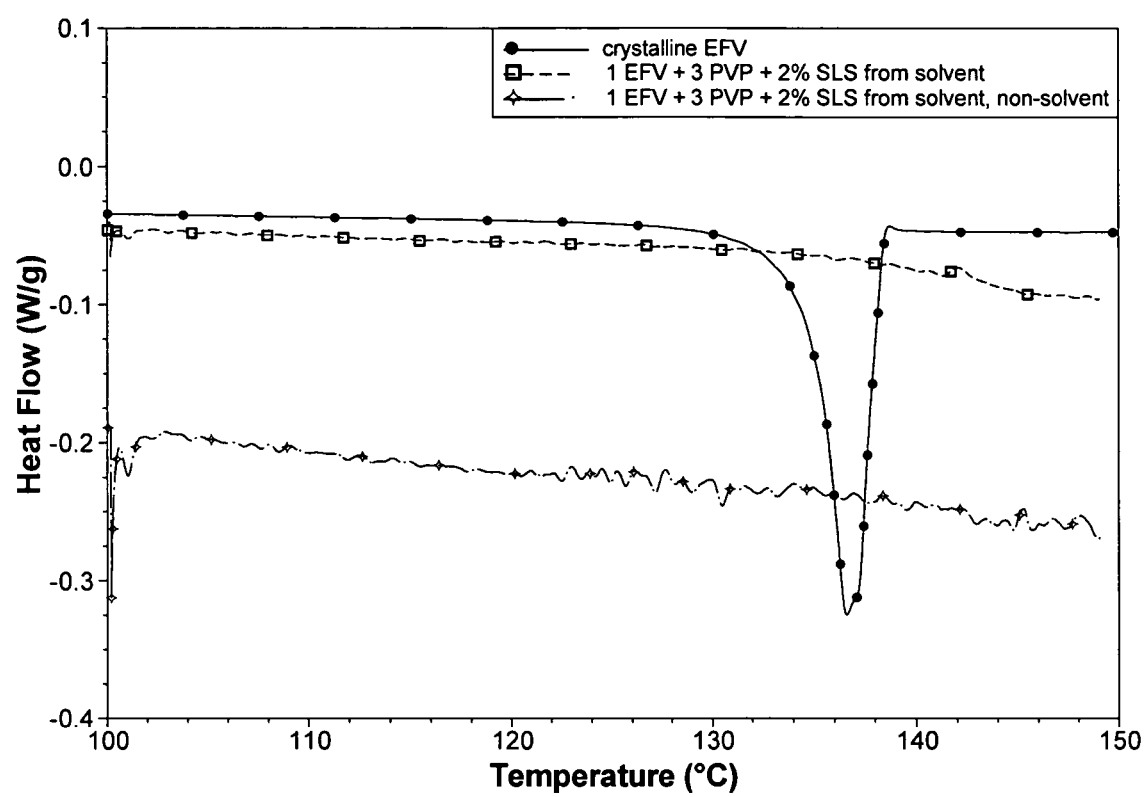
FIG. 5 is a plot of heat flow versus temperature for compositions produced in accordance with Example #5.
Figure 6:
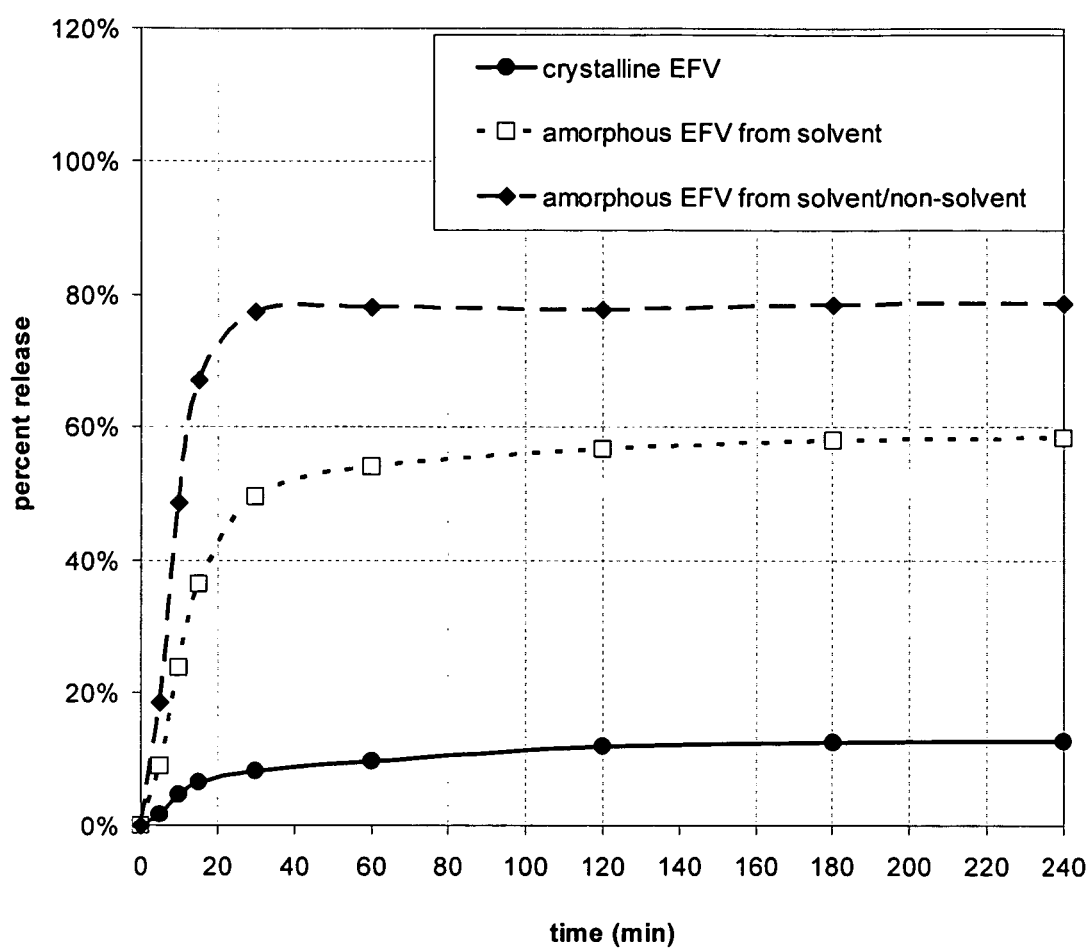
FIG. 6 is a plot of percent release versus time for compositions produced in accordance with Example #5.

The two solutions were spray dried under identical conditions on an SD-Micro® (Niro, Inc.) spray dryer to yield spray dried powders.
2. The two compositions were analyzed for EFV crystallinity using differential scanning calorimetry. Both powders were amorphous, as indicated by the absence of an EFV melt endotherm (FIG. 5).
3. Both amorphous EFV compositions achieved faster rate of release and higher maximum concentration in USP water than the crystalline form as tested in USP apparatus II (paddles). Surprisingly, the spray dried powder from the solvent/non-solvent solution attained a faster release and higher extent of release than the powder spray dried from the solvent only solution (FIG. 6).

J. Example #6

Figure 7:
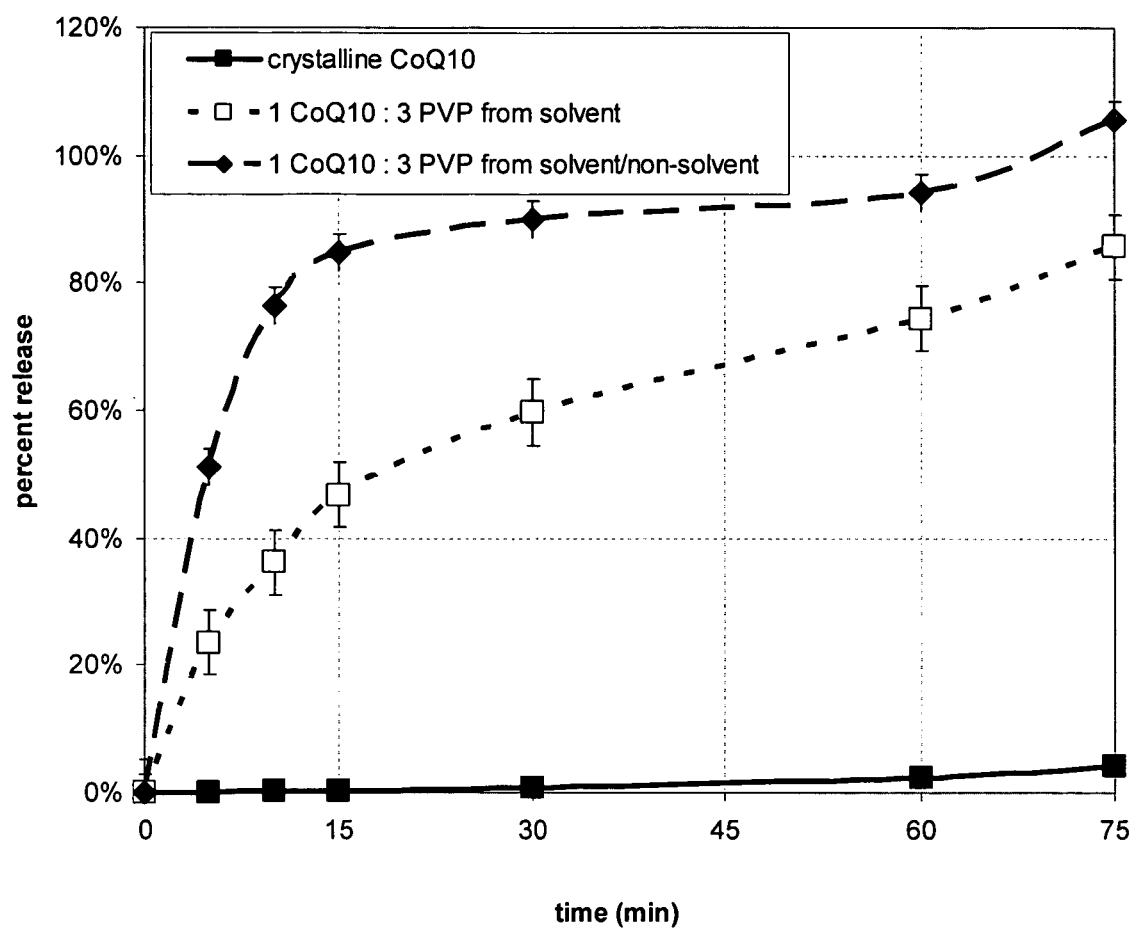
FIG. 7 is a plot of percent release versus time for compositions produced in accordance with Example #6.

1. Coenzyme Q10 (CoQ10) was spray dried with polyvinylpyrrolidone (PVP) (Plasdone® K-29/32, International Specialty Products) in the ratio 1 CoQ10:3 PVP at 20% total solids. Two spray dried powders were produced, one from 100% dichloromethane (DCM) and the other from a blend of 80% DCM, 20% acetone. CoQ10 is soluble in both DCM and acetone, while PVP is only soluble in DCM. All other spray drying conditions remained the same.
2. Sample analysis included USP dissolution using apparatus II (paddles). All samples were hand-filled into size 1 gelatin capsules. The bath temperature was 37° C. with a paddle speed of 50 rpm for the first 60 minutes and then 200 rpm for an additional 15 minutes. The dissolution media contained 2% Cremophor® EL (BASF Corp.), and 4% Acconon® MC8 (Abitec Corp.). Test results are provided in Table 1.
3. Both spray dried powders exhibited enhanced dissolution properties compared to crystalline CoQ10 (as received) (FIG. 7). The change in solvent system affected dissolution behavior, in that powder from solvent/non-solvent solution attained remarkably faster and higher release and extent. It is surprising that the time for 50% CoQ10 dissolution ($t_{50\%}$) was shortened from 18 minutes (100% solvent) to 5 minutes (solvent/non-solvent blend). Similarly, the time for 80% CoQ10 dissolution ($t_{80\%}$) was shortened from 68 minutes to 12 minutes by the switch from 100% solvent to the solvent/non-solvent blend.

Figure 8A:
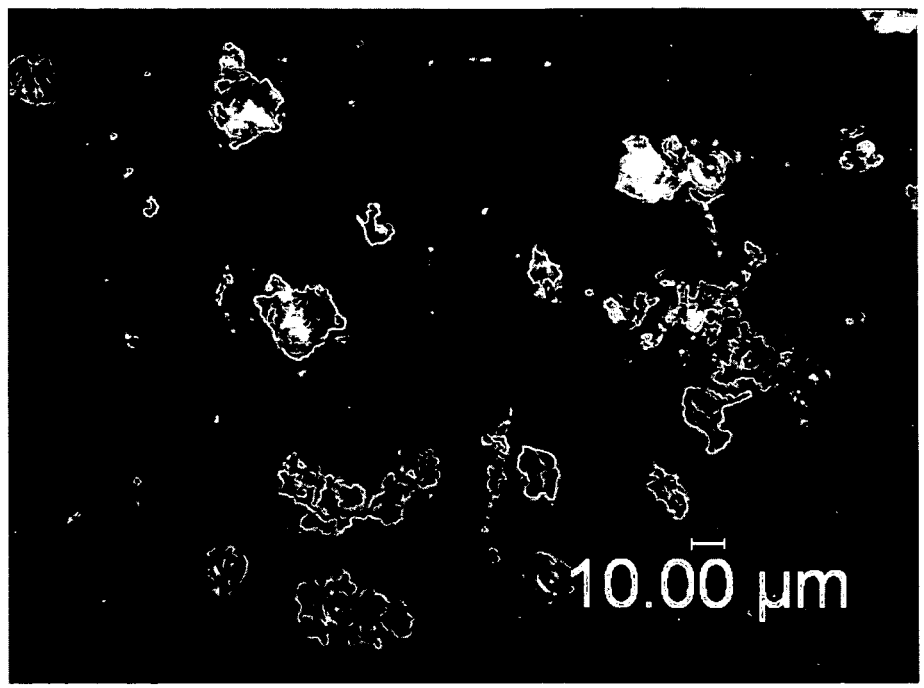
FIGS. 8A-B are photomicrograph images of particles produced in accordance with Example #6.
Figure 8B:
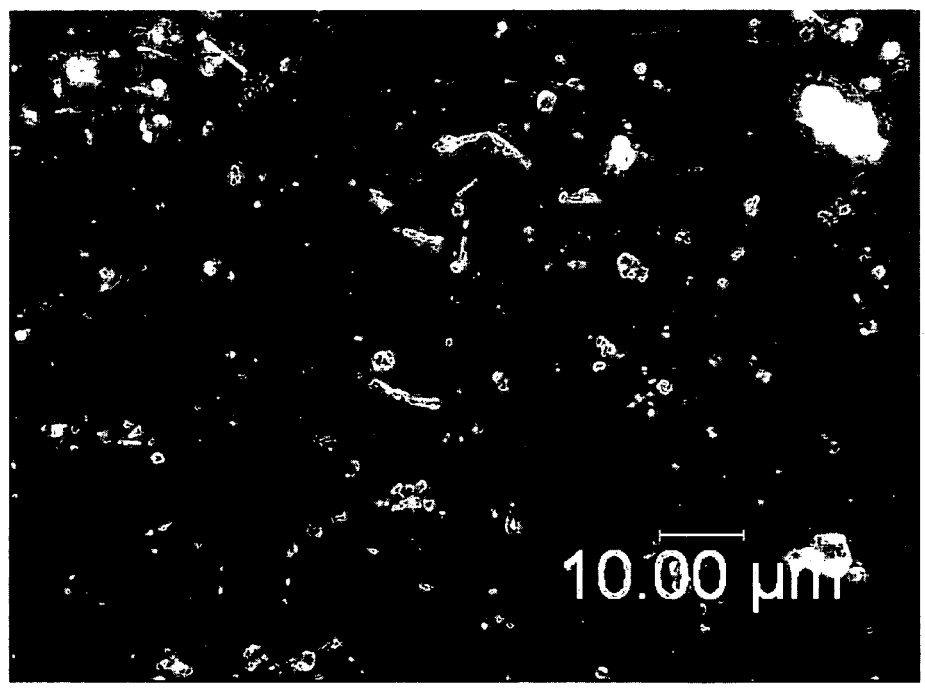
Figure 9:
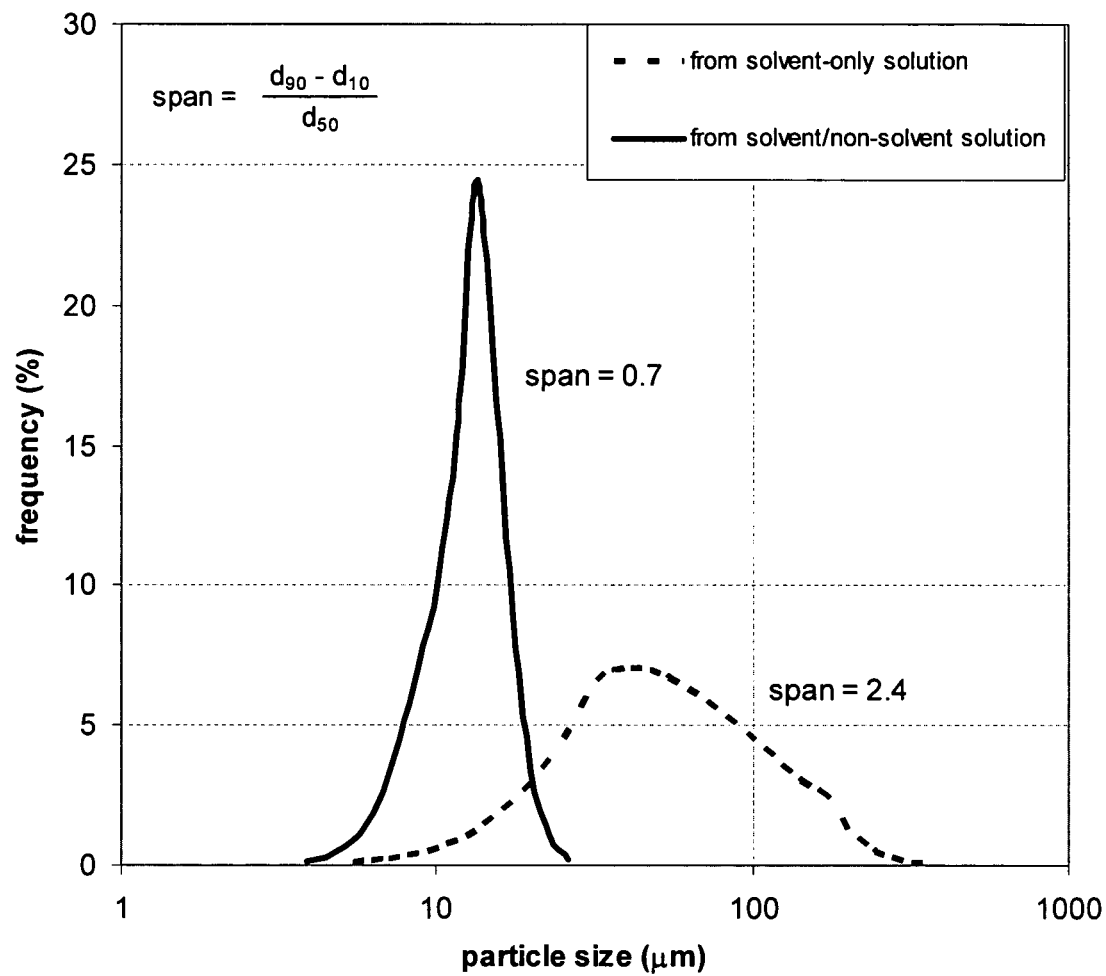
FIG. 9 is a plot of frequency versus particle size for particles produced in accordance with Example #6.

4. Particles from solvent solution were spherical/globular (FIG. 8A), while smaller, thread-like particles formed from the solvent/non-solvent blend (FIG. 8B). The change from solvent to solvent/non-solvent also reduced the particle size distribution (FIG. 9), as indicated by a reduced span (Table 1).

Figure 10:
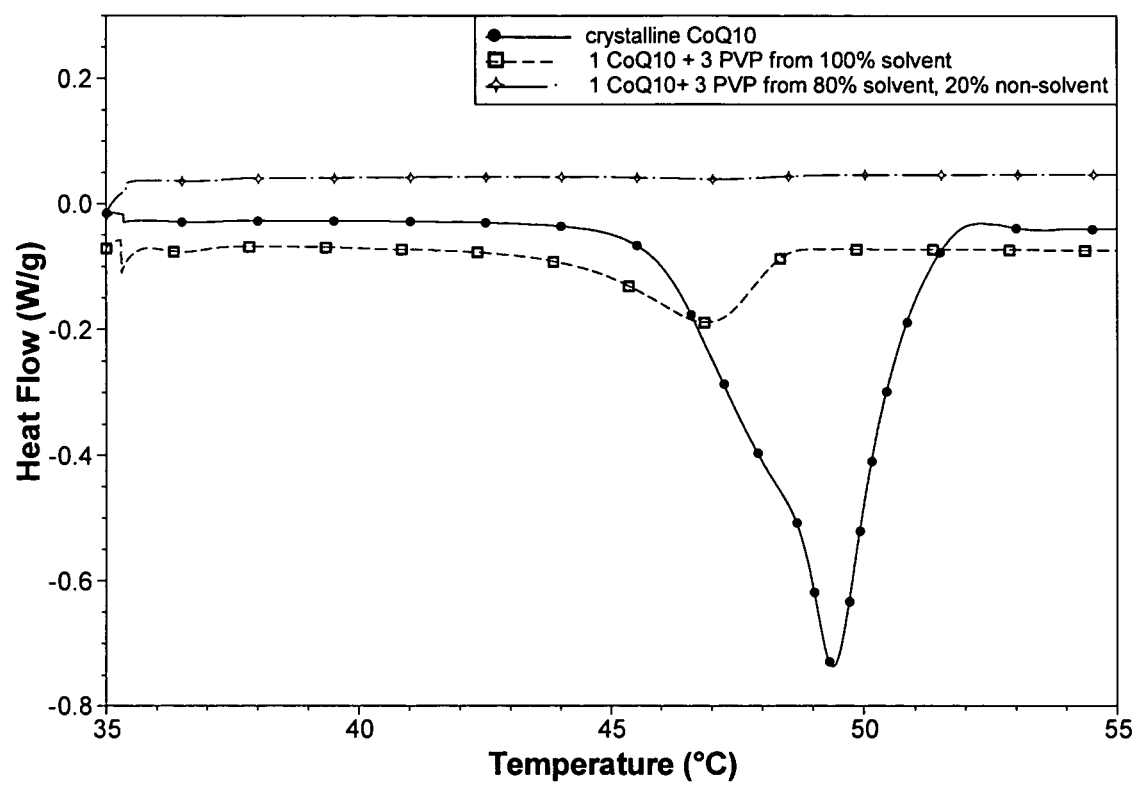
FIG. 10 is a plot of heat flow versus temperature for compositions produced in accordance with Example #6.

5. Surprisingly, the change in solvent system also altered the CoQ10 physical chemistry. While both products were less crystalline than the starting material, the sample prepared from the solvent/non-solvent blend was amorphous, while significant crystallinity was measured in the powder spray dried sprayed from 100% DCM (FIG. 10). Other advantages of the solvent/non-solvent blend approach include lower residual solvent content and higher density.

TABLE 1

Characteristics of CoQ10 sprayed dried from solvent and solvent/non-solvent solutions.

| property | CoQ10 (as received) | spray dried powder | |
| --- | --- | --- | --- |
| | | from solvent | from solvent/non-solvent |
| crystallinity* | 100% | 72% | 3% |
| max. CoQ10 release | 4.3% | 85.8% | 100% |
| $t_{50\%}$ | not attained within 75 minutes | 18 min | 5 min |
| $T_{80\%}$ | not attained within 75 minutes | 68 min | 12 min |
| spray dry yield | | 63% | 83% |
| loss on drying at 105° C. | | 3.8% | 2.5% |
| particle morphology | | spherical, globular | fine fragmented threads and microspheres |
| median particle size: $d_{50}$ (μm) | | 45 μm | 12 μm |
| particle size distribution: span† | | 2.4 | 0.7 |
| bulk density (g/mL) | | 0.132 | 0.154 |
| tapped$_{1250}$ density (g/mL) | | 0.179 | 0.216 |

*As measured by MDSC using heat-only conditions with aluminum, hermetic pans.
†As measured by laser scattering method in air, span = $(d_{90} - d_{10})/d_{50}$

What is claimed is:

1. A method for preparing a spray dried composition having residual solvent content of less than about 10% by weight comprising:
    a) providing a mixture comprising a polymer and an active agent in a blend of a solvent and non-solvent for the polymer wherein the solvent has a lower boiling point than the non-solvent, wherein the polymer comprises polyvinyl pyrrolidone, the solvent comprises dichloromethane and the non-solvent comprises acetone;
    b) distributing the mixture into either droplets or granules, and
    c) evaporating the solvent and non-solvent mixture to form particles having an average size of from about 0.5 μm to about 5000 μm; wherein the active agent is selected from the group consisting of abacavir sulfate, acebutolol, acetaminophen, acemetacin acetylcysteine, acetylsalicylic acid, acyclovir, adefovir dipivoxil, alprazolam, albumin, alfacalcidol, allantoin, allopurinol, ambroxol, amikacin, amiloride, aminoacetic acid, amiodarone, amitriptyline, amlodipine, amoxicillin, amoxicillin trihydrate, amiodarone hydrochloride, amphotericin B, ampicillin, amprenavir, aprepitant, anastrozole, ascorbic acid, aspartame, astemizole, atazanavir sulfate, atenolol, atorvastatin calcium, azathioprine, azithromycin, azithromycin dihydrate, beclomethasone, benserazide, benzalkonium hydroxide, benzocaine, benzoic acid, betametasone, bezafibrate, biotin, biperiden, bisoprolol, bosentan, bromazepam, bromhexine, bromocriptine, budesonide, bufexamac, buflomedil, buspirone, caffeine, camphor, candesartan cilexetil, captopril, carbamazepine, carbidopa, carboplatin, carvedilol, cefachlor, cefalexin, cefadroxil, cefazolin, cefdinir, cefixime, cefotaxime, ceftazidime, ceftriaxone, cefuroxime, celecoxib, chloramphenicol, chlorhexidine, chlorpheniramine, chlortalidone, choline, cilastatin, cilostazol, cimetidine, ciprofloxacin, cisapride, cisplatin, citalopram hydrobromide, clarithromycin, clavulanic acid, clomipramine, clonazepam, clonidine, clopidogrel bisulfate, clotrimazole, clozapine, codeine, colestyramine, coenzyme Q10, cromoglycic acid, cyanocobalamin, cyclosporin, cyproterone, danazole, delavirdine mesylate, desipramine, desloratadine, desmopressin, desogestrel, dexamethasone, dexpanthenol, dextromethorphan, dextropropoxiphene, diazepam, diclofenac, digoxin, dihydrocodeine, dihydroergotamine, diltiazem, diphenhydramine, dipyridamole, dipyrone, disopyramide, docetaxel, domperidone, dopamine, doxycycline, doxorubicin hydrochloride, dronabinol, dutasteride, efavirenz, eletriptan hydrobromide, emtricitabine, enalapril, enrofloxacin, entacapone, ephedrine, epinephrine, eplerenone, eprosartan mesylate, ergocalciferol, ergoloid mesylate, ergotamine tartrate, erythromycin, escitalopram oxalate, estradiol, ethinylestradiol, etoposide, exemestane, ezetimibe, famotidine, felodipine, fenofibrate, fenoterol, fentanyl, fexofenadine hydrochloride, finasteride, flavin mononucleotide, fluconazole, flunarizine, fluorouracil, fluoxetine, flurbiprofen, fluphenazine hydrochloride, flutamide, fluticasone propionate, fluvastatin, fosamprenavir, fosamprenavir calcium, furosemide, gabapentin, galantamine hydrobromide, ganciclovir, gemfibrozil, gentamicin, *Ginkgo biloba*, glibenclamide, glimepiride, glipizide, *Glycyrrhiza glabra*, glyburide, guaifenesin, guanabenz, haloperidol, heparin, hyaluronic acid, hydrochlorothiazide, hydrocodone, hydrocortisone, hydromorphone, hydroxytetracycline, ipratropium hydroxide, ibuprofen, idarubicin, imipenem, imipramine hydrochloride, indinavir sulfate, indomethacin, iohexol, iopamidol, irinotecan, isosorbide dinitrate, irbesartan, isosorbide mononitrate, isotretinoin, isradipine, itraconazole, ketotifen, ketoconazole, ketoprofen, ketorolac, labetalol, lactulose, lamivudine, lamotrigine, lansoprazole, lecithin, levetiracetam, levocarnitine, levodopa, levoglutamide, levonorgestrel, levothyroxine, lidocaine, lipase, lisinopril, loperamide, lopinavir, loratadine, lorazepam, lovastatin, medroxyprogesterone, meloxicam, melphalan, menthol, mercaptopurine, mesalamine, methotrexate methyldopa, N-methylephedrine, methylprednisolone, metoclopramide, metolazone, metoprolol, miconazole, midazolam, minocycline, minoxidil, misoprostol, mitotane, modafanil, mometasone, morphine, mosapride, multivitamins and minerals, nabumetone, nadolol, naftidrofuryl, naproxen, nefazodone, nelfinavir mesylate, neomycin, nevirapine, nicardipine hydrochloride, nicergoline, nicotinamide, nicotine, nicotinic acid, nifedipine, nimodipine, nisoldipine, nitrendipine, nizatidine, norethisterone, norfloxacin, norgestrel, nortriptyline, nystatin, ofloxacin, olanzepine, olmesartan medoxomil, omeprazole, ondansetron, orlistat, oxcarbazepine, paclitaxel, pancreatin, panthenol, pantoprazole, pantothenic acid, paracetamol, paroxetine hydrochloride, penicillin G, penicillin V, perphenazine, phenobarbital, phenylephrine, phenylpropanolamine, phenytoin, pimecrolimus, pimozide, pioglitazone hydrochloride, piroxicam, polymyxin B, povidone-iodine, pravastatin sodium, prazepam, prazosin, prednisolone, prednisone, proglumetacin, propafenone hydrochloride, propranolol, propofol, pseudoephedrine, pyridoxine, quinaprile hydrochloride, quinidine, raloxifine hydrochloride, ramipril, ranitidine, reserpine, retinol, ribavirin, riboflavin, rifampicin, risperidone, ritonavir, rosuvastatin calcium, rutoside, saccharin, salbutamol, salcatonin, salicylic acid, salmetrol xinafoate, saquinavir, sertaline, sildenafil citrate, simvastatin, sirolimus, somatropin, sotalol, spironolactone, stavudine, sucralfate, sulbactam, sulfamethoxazole, sulphasalazine, sulpiride, tacrolimus, tadalafil, tamoxifen, tamsulosin hydrochloride, tegafur, tenofovir disoproxil fumarate, tenoxicam, teprenone, terazosin, terbinafine hydrochloride, tegaserod maleate, telmisartan, terbutaline, terfenadine, thalidomide, theophylline, thiamine, tiaprofenic acid, ticlopidine, timolol, tizanidine hydrochloride, topiramate, trandolapril, tranexamic acid, tretinoin, triamcinolone acetonide, triamterene, triazolam, trimethoprim, troxerutin, uracil, valdecoxib, valgancyclovir hydrochloride, valproic acid, valrubicin, valsartan, vancomycin, verapamil, vardenafil hydrochloride, vitamin E, zafirlukast, zalcitabine, zalephon, zidovudine, ziprasidone, zolpidem tartrate, zonisamide, zotepine and mixtures thereof, and wherein the resulting spray dried composition has said residual solvent content of less than about 10% by weight.

2. The method of claim 1 wherein the mixture further comprises one or more pharmaceutically acceptable ingredients.

3. The method of claim 1 wherein the polymer is selected from the group consisting of: aliphatic polyesters, carboxyalkylcelluloses, alkylcelluloses, gelatins, hydroxyalkylcelluloses, hydroxyalkylalkylcelluloses, hydroxyalkylalkylcellulose derivatives, polyamines, polyethylene glycols, methacrylic acid polymers and copolymers, homo- and copolymers of N-vinyl pyrrolidone, homo- and copolymers of vinyllactam, starches, polysaccharides, poly glycols, polyvinyl esters, refined/modified shellac and mixtures thereof.

4. The method of claim 1 wherein the solvent and non-solvent are present at a ratio of from about 5% solvent: 95% non-solvent to about 95% solvent:5% non-solvent by weight.

5. The method of claim 4 wherein the ratio of solvent to non-solvent is selected such that the polymer is dissolved in the mixture.

6. The method of claim 1 wherein the concentration of the polymer in the mixture is from about 1% to about 90% by weight.

7. The method of claim 1 wherein said solid composition contains less residual solvent immediately after spray drying or granulation than a solid composition produced from a mixture containing solvent alone.

8. The method of claim 7 wherein said solid composition contains less than 2% residual solvent by weight.

9. The method of claim 1 wherein said solid materials comprise particles and said particles have a higher density than particles produced from a mixture containing solvent alone.

10. The method of claim 1 wherein the mixture has a solids content of more than 1% by weight.

11. The method of claim 1 wherein the active agent is rendered into an amorphous state using less polymer than can be achieved using a mixture without a non-solvent.

12. The method of claim 1 wherein the active agent exhibits increased dissolution compared to a control composition prepared from a mixture without a non-solvent.

13. The method of claim 1 wherein the active agent exhibits an increased rate of dissolution compared to a control composition prepared from a mixture without a non-solvent.

14. The method of claim 1 wherein the active agent exhibits an increased extent of dissolution compared to a control composition prepared from a mixture without a non-solvent.

15. The method of claim 1 further comprising depositing said droplets onto a particulate substrate.

16. A composition comprising particles produced in accordance with claim 1.

17. A pharmaceutical composition comprising the composition of claim 16.

18. The pharmaceutical composition of claim 16 in the form of an oral, solid-dosage form.

19. A spray dried composition produced by the method of claim 13.

* * * * *